United States Patent
Maeda et al.

(10) Patent No.: US 9,206,138 B2
(45) Date of Patent: Dec. 8, 2015

(54) CRYSTAL CONTAINING UNSATURATED CARBOXYLIC ACID AMIDE COMPOUND AND METHOD FOR PRODUCING SAME

(71) Applicant: DAICEL CORPORATION, Osaka-shi, Osaka (JP)

(72) Inventors: Yukitsugu Maeda, Myoko (JP); Takafumi Imoto, Myoko (JP); Yasuyuki Akai, Himeji (JP); Kouhei Fujita, Himeji (JP); Shinya Sahara, Myoko (JP)

(73) Assignee: Daicel Corporation, Osaka (JP)

( * ) Notice: Subject to any disclaimer, the term of this patent is extended or adjusted under 35 U.S.C. 154(b) by 0 days.

(21) Appl. No.: 14/417,769

(22) PCT Filed: Aug. 5, 2013

(86) PCT No.: PCT/JP2013/071146
§ 371 (c)(1),
(2) Date: Jan. 27, 2015

(87) PCT Pub. No.: WO2014/024843
PCT Pub. Date: Feb. 13, 2014

(65) Prior Publication Data
US 2015/0299135 A1    Oct. 22, 2015

(30) Foreign Application Priority Data

Aug. 10, 2012 (JP) .................... 2012-178482
Jul. 3, 2013 (JP) .................... 2013-139981

(51) Int. Cl.
*C07D 233/60* (2006.01)
*C07D 235/18* (2006.01)
*C07D 235/06* (2006.01)

(52) U.S. Cl.
CPC ............ *C07D 233/60* (2013.01); *C07D 235/06* (2013.01); *C07D 235/18* (2013.01)

(58) Field of Classification Search
CPC ... C07D 233/60; C07D 235/06; C07D 235/18
See application file for complete search history.

(56) References Cited

U.S. PATENT DOCUMENTS

| 4,931,471 A | 6/1990 | Jung et al. |
| 6,017,919 A | 1/2000 | Inaba et al. |

(Continued)

FOREIGN PATENT DOCUMENTS

| EP | 0 887 340 A1 | 12/1998 |
| EP | 2 725 011 A1 | 4/2014 |

(Continued)

OTHER PUBLICATIONS

Written Opinion of the International Searching Authority for International Application No. PCT/JP2013/071146, dated Sep. 3, 2013.*

(Continued)

*Primary Examiner* — Matthew Coughlin
(74) *Attorney, Agent, or Firm* — Birch, Stewart, Kolasch & Birch, LLP (57) ABSTRACT

Provided is a high-purity crystal of an unsaturated carboxylic acid amide compound which is useful as or for fine chemicals such as pharmaceuticals, agricultural chemicals, polymeric materials, functional materials, and intermediates of them.
The crystal includes an unsaturated carboxylic acid amide compound represented by Formula (1) in an amount of 95 percent by area or more. In X-ray diffraction, the crystal exhibits peaks at 2θ in the range of 29.0 to 30.0 and in at least one range selected from 6.0 to 8.0, 12.0 to 13.5, and 16.5 to 17.5 and exhibits approximately no peak at 2θ in the range of 14.0 to 15.0.

[Chem. 1]

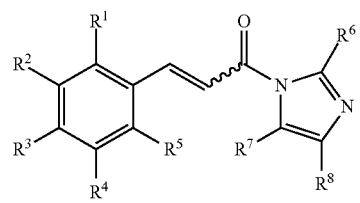

(1)

4 Claims, 1 Drawing Sheet

(56) References Cited

U.S. PATENT DOCUMENTS

| | | |
|---|---|---|
| 2003/0161860 A1 | 8/2003 | Taneja et al. |
| 2010/0204280 A1 | 8/2010 | Pardin et al. |
| 2011/0086311 A1 | 4/2011 | Katayama et al. |
| 2014/0221649 A1 | 8/2014 | Shiota et al. |

FOREIGN PATENT DOCUMENTS

| | | |
|---|---|---|
| JP | 62-502749 A | 10/1987 |
| JP | 2002-187868 A | 7/2002 |
| JP | 2005-517737 A | 6/2005 |
| JP | 2009-263543 A | 11/2009 |
| WO | WO 97/29079 A1 | 8/1997 |
| WO | WO 03/070713 A1 | 8/2003 |
| WO | WO 2008/144933 A1 | 12/2008 |
| WO | WO 2009/123122 A1 | 10/2009 |
| WO | WO 2012/176621 A1 | 12/2012 |
| WO | WO 2012/176693 A1 | 12/2012 |

OTHER PUBLICATIONS

Alabaster et al., "Synthesis of 6-(3-Aryl-2-propenyl)-2,3-dihydro-5-hydroxybenzofuran Derivatives by Cross Coupling Reactions", Synthesis, Aug. 1989, pp. 598-603.

Imashiro et al., "A Catalytic Asymmetric Synthesis of Chiral Glycidic Acid Derivatives through Chiral Dioxirane-Mediated Catalytic Asymmetric Epoxidation of Cinnamic Acid Derivatives", Journal of Organic Chemistry, 2004, vol. 69, pp. 4216-4226.

International Search Report, mailed Sep. 3, 2013, issued in PCT/JP2013/071146.

Ohta et al., "Esterase-Like Activity of Human Serum Albumin II: Reaction with N-trans-Cinnamoylimidazoles", Journal of Pharmaceutical Sciences, vol. 72, No. 4, Apr. 1983, pp. 385-388.

Papa et al., "The Analgesic Activity of N,N-Dialkyl Amides", Journal of American Chemical Society, vol. 72, Sep. 1950, pp. 3885-3886.

\* cited by examiner

CRYSTAL CONTAINING UNSATURATED CARBOXYLIC ACID AMIDE COMPOUND AND METHOD FOR PRODUCING SAME

TECHNICAL FIELD

The present invention generally relates to crystals including unsaturated carboxylic acid amide compounds, and methods for producing the crystals. The unsaturated carboxylic acid amide compounds are useful as fine chemicals such as pharmaceuticals, agricultural chemicals, polymeric materials, functional materials, and intermediates of them.

BACKGROUND ART

Unsaturated carboxylic acid amide compounds have been produced typically by methods in which an unsaturated carboxylic acid is dehydratively condensed with an amine. Patent Literature (PTL) 1 describes a method for producing 2-hydroxycinnamamide. In the method, 2-hydroxycinnamic acid is dehydratively condensed with an amine using carbodiimide as a dehydrating-condensing agent. Non Patent Literature (NPL) 1 describes a method for producing 4-methoxycinnamamide. In the method, 4-methoxycinnamic acid is dehydratively condensed with an amine using N,N-carbonyldiimidazole as a dehydrating-condensing agent. Unfortunately, the dehydrating-condensing agents used in the methods are expensive and may cause a severe allergic reaction. Alternatively, such unsaturated carboxylic acid amide compounds have been produced by a method of hydrating an unsaturated carboxylic acid nitrile. Disadvantageously, the method suffers from deterioration in reaction selectivity in some kinds of the unsaturated carboxylic acid moiety. For these reasons, the above-mentioned methods are employed with difficulty as methods for industrially producing unsaturated carboxylic acid amide compounds.

Under such circumstances, unsaturated carboxylic acid amide compounds are synthetically prepared most generally by methods in which an unsaturated carboxylic acid is allowed to react with thionyl chloride to give an unsaturated carboxylic acid chloride, and the prepared unsaturated carboxylic acid chloride is allowed to react with an amine. In a method described in NPL 2, an unsaturated carboxylic acid is mixed with thionyl chloride in an amount 8.6 times the mole of the unsaturated carboxylic acid with cooling and, after the initiation of reaction, the mixture is heated to reflux to give an unsaturated carboxylic acid chloride. However, an unsaturated carboxylic acid amide compound prepared by the method included large amounts of organochlorine compounds derived from thionyl chloride.

Independently, high-performance (highly functional) materials include photosensitive high-performance materials (resist materials) for use in the production of electrical and electronic components. Among them, those requiring particularly high reliability include semiconductor encapsulating materials, packaging materials typically for semiconductor devices and MEMS (micro electro mechanical systems), and photosensitive materials for semiconductor devices, liquid crystal displays, and MEMS. These materials should include ingredients with higher and higher purity. Of impurities or by-products, chlorine-containing compounds are known to significantly affect the performance of electrical and electronic components. PTL 2 discloses that a halogen atom contained in by-products becomes a halogen anion upon exposure (light irradiation), thus reduces the effect of an acid generator, and lowers the sensitivity. PTL 3 discloses as follows. Assume that a compound contains, as impurities, large amounts of organochlorine compounds such as hydrolyzable chlorine that liberates a chlorine ion upon moisture absorption. This compound, when used in the production of an electrical/electronic component, causes the electrical/electronic component to be susceptible to corrosion and/or a break of interconnections and deterioration in insulation quality and to have inferior reliability.

To prevent this, demands have been made to provide a method for producing a crystal including a high-purity unsaturated carboxylic acid amide compound and having a very low content of impurities such as organochlorine compounds. In addition, demands have also been made to provide a method without the use of aromatic hydrocarbon solvents such as toluene, because the aromatic hydrocarbon solvents may adversely affect the environment.

CITATION LIST

Patent Literature

PTL 1: PCT International Publication Number WO2009/123122
PTL 2: Japanese Unexamined Patent Application Publication (JP-A) No. 2002-187868
PTL 3: JP-A No. 2009-263543

Non Patent Literature

NPL 1: *Journal of Organic Chemistry*, volume 69, p. 4216 (2004)
NPL 2: *Journal of American Chemical Society*, volume 72, p. 3885 (1950)
NPL 3: *Synthesis*, p. 598 (1989)

SUMMARY OF INVENTION

Technical Problem

Accordingly, it is an object of the present invention to provide a crystal of an unsaturated carboxylic acid amide compound, where the crystal has a high purity and is useful as or for fine chemicals such as pharmaceuticals, agricultural chemicals, polymeric materials, functional materials, and intermediates of them.

It is another object of the present invention to provide a method for efficiently producing a high-purity crystal of an unsaturated carboxylic acid amide compound without using aromatic hydrocarbon solvents that may adversely affect the environment.

Solution to Problem

After intensive investigations to achieve the objects, the present inventors have obtained findings 1 to 4 as follows.

1. Assume that, in a production method, an unsaturated carboxylic acid is chlorinated with thionyl chloride to give an unsaturated carboxylic acid chloride, and the unsaturated carboxylic acid chloride is allowed to react with an imidazole compound to give an unsaturated carboxylic acid amide compound as a reaction product. This production method, when performed so as to use thionyl chloride in an amount controlled within a specific range, or to remove chlorine-containing compounds using an adsorbent after the reactions, can give an unsaturated carboxylic acid amide compound having a very low content of such chlorine-containing compounds.

2. The reaction product, when being washed with water and then subjected to crystallization, can give a high-purity crystal of the unsaturated carboxylic acid amide compound.

3. Assume that an ester solvent that loads a small environmental burden is used instead of aromatic hydrocarbon solvents such as toluene; and that the reaction product after washing with water in this case is subjected to crystallization without undergoing dehydration to give a crystal. The resulting crystal has a high water content and is susceptible to hydrolysis when subsequently subjected to drying treatment over a long period of time. The crystal is hardly prevented from deterioration in quality upon industrial production. In addition, the crystal readily scatters and is attached to the vessel wall, thus often causing losses.

4. The reaction product after washing, when dehydrated and then crystallized, gives a crystal that is not hydrolyzed even upon subsequent drying treatment over a long period of time and has such properties as to resist scattering and attachment to the vessel wall.

The present invention has been made based on these findings.

Specifically, the present invention provides, in one aspect, a crystal including an unsaturated carboxylic acid amide compound represented by Formula (1) in an amount of 95 percent by area or more. In X-ray diffraction, the crystal exhibits a peak at 2θ in the range of from 29.0 to 30.0 and a peak at 2θ in at least one range selected from the group consisting of 6.0 to 8.0, 12.0 to 13.5, and 16.5 to 17.5. The crystal exhibits, in X-ray diffraction, approximately no peak at 2θ in the range of 14.0 to 15.0. Formula (1) is expressed as follows:

[Chem. 1]

(1)

where $R^1$ to $R^5$ are identical or different groups independently selected from hydrogen, alkyl, hydroxyl, alkoxy, and nitro. At least two of $R^1$ to $R^5$ may be linked to form a ring together with carbon atoms constituting the specified aromatic ring. $R^6$, $R^7$, and $R^8$ are identical or different groups independently selected from hydrogen, alkyl, and aryl. $R^7$ and $R^8$ may be linked to form a ring together with carbon atoms constituting the specified imidazole ring. The amount of the unsaturated carboxylic acid amide compound is measured using high-performance liquid chromatography under analysis conditions as follows. Specifically, the high-performance liquid chromatographic is performed using an INERTSIL® ODS3 column, a mobile phase including a component "A" of a 50 mM $KH_2PO_4/K_2HPO_4$ (pH=7) aqueous solution and a component "B" of acetonitrile, in an isocratic (A:B=50%:50% (v/v)) pump mode, at an UV wavelength of 220 nm, an injection volume of 5 μm, a column temperature of 40° C., and a flow rate of 1.0 mL/min.

In the crystal, the unsaturated carboxylic acid amide compound may include at least one compound selected from the group consisting of compounds represented by Formulae (1-1) to (1-6):

[Chem. 2]

(1-1)

(1-2)

(1-3)

(1-4)

(1-5)

(1-6)

The present invention provides, in another aspect, a method for producing a crystal. The method includes a reaction step 1 (step a)), a reaction step 2 (step b)), and a purification step (step c)) to give the crystal as mentioned above. In the reaction step 1, an unsaturated carboxylic acid is chlorinated with thionyl chloride to give a compound represented by Formula (3). In the reaction step 2, the prepared compound represented by Formula (3) is allowed to react with an imidazole compound represented by Formula (4) to give an unsaturated carboxylic acid amide compound represented by Formula (1) as a reaction product. In the purification step, the reaction product is purified. The reaction step 1 is performed in the presence of an ester solvent. In the method, the thionyl chloride in the reaction step 1 is used in an amount of from 0.5 to 3.0 times the mole of the unsaturated carboxylic acid represented by Formula (2), and/or, a chlorine-containing compound is separated and removed using an adsorbent in the purification step. In the purification step, water is added to the reaction system to wash the reaction product, the reaction product after washing is dehydrated to a water content of 2.0 percent by weight or less, and then subjected to crystallization. Formulae (2), (3), (4), and (1) are expressed as follows:

[Chem. 3]

(2)

where $R^1$ to $R^5$ are identical or different groups independently selected from hydrogen, alkyl, hydroxyl, alkoxy, and nitro. At least two of $R^1$ to $R^5$ may be linked to form a ring together with carbon atoms constituting the specified aromatic ring,

[Chem. 4]

(3)

where $R^1$ to $R^5$ are as defined above,

[Chem. 5]

(4)

where $R^6$, $R^7$, and $R^8$ are identical or different groups independently selected from hydrogen, alkyl, and, aryl. $R^7$ and $R^8$ may be linked to form a ring together with carbon atoms constituting the specified imidazole ring,

[Chem. 6]

(1)

where $R^1$ to $R^8$ are as defined above.

Advantageous Effects of Invention

The crystal according to the present invention includes the unsaturated carboxylic acid amide compound represented by Formula (1) in an amount of 95 percent by area or more and has a high purity. In X-ray diffraction, the crystal exhibits peaks at 2θ in the specific ranges and exhibits approximately no peak at 2θ in the specific range. The crystal therefore has such properties as to resist scattering and attachment to the vessel wall. In addition, the production method according to the present invention can stably produce the crystal having the properties even upon industrial production (i.e., upon large-scale production). For these reasons, the crystal according to the present invention is particularly useful as raw materials for industrial products. The crystal is advantageously usable as or for pharmaceuticals, agricultural chemicals, polymeric materials, high-performance materials, and intermediates of them. The high-performance materials are exemplified by photosensitive high-performance materials (resist materials) for use in the production of electrical and electronic components. Among them, the crystal is particularly preferably usable as or for such materials requiring high reliability, such as semiconductor encapsulating materials, packaging materials typically for semiconductor devices and MEMS (micro electro mechanical systems), and photosensitive materials for semiconductor devices, liquid crystal displays, and MEMS.

DESCRIPTION OF EMBODIMENTS

Crystal

The crystal according to the present invention contains an unsaturated carboxylic acid amide compound represented by Formula (1):

[Chem. 7]

(1)

where $R^1$ to $R^5$ are identical or different groups independently selected from hydrogen, alkyl, hydroxyl, alkoxy, and nitro, where at least two of $R^1$ to $R^5$ may be linked to form a ring together with carbon atoms constituting the specified aromatic ring. $R^6$, $R^7$, and $R^8$ are identical or different groups independently selected from hydrogen, alkyl, and aryl, where $R^7$ and $R^8$ may be linked to form a ring together with carbon atoms constituting the specified imidazole ring.

As $R^1$ to $R^5$, the alkyl is exemplified by alkyl containing 1 to about 4 carbon atoms, such as methyl, ethyl, propyl, isopropyl, and butyl. The alkoxy is exemplified by alkoxy containing 1 to about 6 carbon atoms, such as methoxy, ethoxy, isopropoxy, butoxy, isobutoxy, sec-butoxy, tert-butoxy, and pentoxy. In an embodiment, at least two of $R^1$ to $R^5$ are linked to form a ring together with carbon atoms constituting the specified aromatic ring. The formed ring is exemplified by aromatic rings containing about 6 to about 20 carbon atoms, such as benzene, naphthalene, and anthracene rings, of which those containing 6 to 14 carbon atoms are preferred; hydrocarbon rings (e.g., cycloalkane rings, cycloalkene rings, and bridged carbon rings) containing 3 to about 20 members, such as cyclobutane, cyclopentane, cyclohexane, cyclohexene, cyclooctane, cyclododecane, adamantane, norbornane, and norbornene rings, of which those containing 3 to 15 members are preferred, and those containing 5 to 12 members are particularly preferred. Of the compounds represented by Formula (1), preferred in the present invention are compounds in which $R^1$, $R^2$, $R^4$, and $R^5$ are hydrogen, and $R^3$ is $C_1$-$C_6$ alkoxy (in particular, methoxy). These compounds are preferred because they have excellent absorption sensitivity and can be prepared from easily-available raw materials.

As $R^6$, $R^7$, and $R^8$, the alkyl is exemplified by alkyl containing 1 to about 20 carbon atoms, such as methyl, ethyl, propyl, isopropyl, butyl, isobutyl, s-butyl, t-butyl, pentyl, hexyl, decyl, and dodecyl, of which those containing 1 to 10 carbon atoms are preferred. The aryl is exemplified by aryl containing about 6 to about 20 carbon atoms, such as phenyl and naphthyl, of which those containing 6 to 14 carbon atoms are preferred.

In an embodiment, $R^7$ and $R^8$ are linked to form a ring together with carbon atoms constituting the imidazole ring. The formed ring is exemplified by aromatic rings such as benzene ring. The ring may have one or more substituents. The substituents are exemplified by alkyl containing 1 to about 3 carbon atoms, such as methyl, ethyl, and propyl; and aryl containing about 6 to about 20 carbon atoms, such as phenyl and naphthyl, of which those containing 6 to 14 carbon atoms are preferred.

Specifically, the unsaturated carboxylic acid amide compound represented by Formula (1) is exemplified by compounds represented by Formulae (1-1) to (1-6) below. Among them, the crystal according to the present invention preferably includes the compound represented by Formula (1-1).

[Chem. 8]

The crystal according to the present invention may be produced by a method as follows. The method includes a reaction step 1, a reaction step 2, and a purification step. In the reaction step 1, an unsaturated carboxylic acid represented by Formula (2) is chlorinated with thionyl chloride to give a compound represented by Formula (3). In the reaction step 2, the prepared compound represented by Formula (3) is allowed to react with an imidazole compound represented by Formula (4) to give an unsaturated carboxylic acid amide compound represented by Formula (1) as a reaction product. In the purification step, the reaction product is purified. Formulae (2), (3), (4), and (1) are expressed as follows:

[Chem. 9]

(2)

where $R^1$ to $R^5$ are identical or different groups independently selected from hydrogen, alkyl, hydroxyl, alkoxy, and nitro, where at least two of $R^1$ to $R^5$ may be linked to form a ring together with carbon atoms constituting the specified aromatic ring,

[Chem. 10]

(3)

where $R^1$ to $R^5$ are as defined above,

[Chem. 11]

(4)

where $R^6$, $R^7$, and $R^8$ are identical or different groups independently selected from hydrogen, alkyl, and aryl, where $R^7$ and $R^8$ may be linked to form a ring together with carbon atoms constituting the specified imidazole ring,

[Chem. 12]

(1)

where $R^1$ to $R^8$ are as defined above. The method is performed under conditions 1 to 3 as follows.

1. The reaction step 1 is performed in the presence of an ester solvent.
2. In the method, thionyl chloride is used in an amount 0.5 to 3.0 times the mole of the unsaturated carboxylic acid represented by Formula (2) in the reaction step 1, and/or, a chlorine-containing compound is separated and removed using an adsorbent in the purification step.
3. In the purification step, water is added to the reaction system to wash the reaction product, the reaction product after washing is dehydrated to a water content of 2.0 percent by weight or less, and then subjected to crystallization.

The unsaturated carboxylic acid represented by Formula (2) is exemplified by corresponding compounds of Formula (2) in which $R^1$ to $R^5$ are independently the above-exemplified groups.

The imidazole compound represented by Formula (4) is exemplified by imidazole, 2-methylimidazole, 2-ethyl-4-methylimidazole, 2-phenylimidazole, benzimidazole, and 2-phenylbenzimidazole.

Reaction Step 1

The reaction step 1 is the step of chlorinating the unsaturated carboxylic acid represented by Formula (2) with thionyl chloride to give the compound represented by Formula (3). The thionyl chloride may be used in an amount of from about 0.5 to about 3.0 times, preferably from 0.8 to 2.5 times, more preferably from 0.9 to 1.8 times, particularly preferably from 1.0 to 1.5 times, and most preferably from 1.0 to 1.3 times, the mole of the unsaturated carboxylic acid represented by Formula (2). The thionyl chloride, if used in an amount greater than the range, may readily cause chlorine-containing compounds to be by-produced in larger amounts, and this may cause the resulting product to be used with difficulty as a photosensitive high-performance material. In contrast, the thionyl chloride, if used in an amount less than the range, may readily cause the target compound to be obtained in a lower yield. As used herein the term "chlorine-containing compound(s)" refers to all compounds that contain chlorine and are by-produced by the method for producing an unsaturated carboxylic acid amide compound according to the present invention. Major chlorine-containing compounds are exemplified by chlorinated derivatives (chlorides) of the unsaturated carboxylic acid amide compound represented by Formula (1), and analogues of them.

In the present invention, the chlorination reaction is performed using an ester solvent. Namely, the chlorination reaction is performed in the presence of an ester solvent. The ester solvent is exemplified by ethyl acetate, butyl acetate, and isobutyl acetate. Each of them may be used alone or in combination. The chlorination reaction in the present invention is preferably performed using approximately no aromatic hydrocarbon solvent such as toluene. This is preferred for a lowered influence on the environment. Specifically, aromatic hydrocarbon solvents (e.g., toluene) may be used in a proportion of typically less than 100 percent by weight, preferably 50 percent by weight or less, more preferably 10 percent by weight or less, furthermore preferably 5 percent by weight or less, still more preferably 1 percent by weight or less, particularly preferably 0.1 percent by weight or less, and most preferably zero percent by weight, of the total amount (100 percent by weight) of all solvents to be used in the chlorination reaction.

The solvent may be used in an amount of typically from about 1 to about 100000 parts by weight, preferably from 1 to 10000 parts by weight, particularly preferably from 1 to 10 parts by weight, and most preferably from 2 to 6 parts by weight, per 1 part by weight of the unsaturated carboxylic acid represented by Formula (2), whereas the amount is not critical within such a range as to allow the dissolution or dispersion of reactants and as not to impair properties such as economic efficiency.

The chlorination reaction may be performed typically by adding thionyl chloride dropwise to a system including the unsaturated carboxylic acid represented by Formula (2). The reaction may be performed for a time of from about 0.5 to about 48 hours, preferably from 1 to 36 hours, and particularly preferably from 2 to 24 hours. The dropwise addition of thionyl chloride may be performed at a temperature of typically from 40° C. to the boiling point(s) of substances present in the reaction system, preferably from 55° C. to 120° C., and particularly preferably from 60° C. to 75° C. The reaction after the completion of thionyl chloride dropwise addition may be performed at a temperature of typically from 55° C. up to the boiling point(s) of substances present in the reaction system, preferably from 55° C. to 120° C., and particularly preferably from 60° C. to 75° C. The thionyl chloride dropwise addition and the reaction after the completion of dropwise addition may be performed at identical or different temperatures. The thionyl chloride dropwise addition and the reaction after the completion of dropwise addition, if each performed at a temperature lower than the range, may readily cause the compound represented by Formula (3) to be prepared in a lower yield. In contrast, the thionyl chloride dropwise addition and the reaction after the completion of dropwise addition, if each performed at a temperature higher than the range, may cause chlorine-containing compounds to be by-produced in larger amounts. This may impede the use of the target product as a photosensitive high-performance material.

The chlorination reaction may be performed under any of a pressure (under a load), normal atmospheric pressure, and reduced pressure (typically from about 0.0001 to about 0.1 MPa, and preferably from 0.001 to 0.1 MPa). The reaction is often performed under normal atmospheric pressure or reduced pressure.

In a preferred embodiment of the present invention, the method includes an operation of removing excessive thionyl chloride during or after the completion of the reaction step 1. This is preferred for a lower content of chlorine-containing compounds in the crystal. The excessive thionyl chloride may be removed by a common process or procedure including separation using degassing, extraction, distillation, rectification, molecular distillation, and/or adsorption. The operation as above may be performed continuously or discontinuously (batchwise). The operation may be performed under either of reduced pressure and normal atmospheric pressure.

In another preferred embodiment, the reaction in the reaction step 1 may be performed while continuously separating a by-produced acidic gas from the reaction system, where the acidic gas is exemplified by hydrogen chloride and sulfur dioxide gases. This is preferred for a lower content of chlorine-containing compound in the crystal. The by-produced acidic gas may be separated by a common process including separation typically using degassing, extraction, distillation, rectification, molecular distillation, and/or adsorption. The separation process as above may be performed continuously or discontinuously (batchwise). The (separation) operation may be performed under either of reduced pressure and normal atmospheric pressure.

Reaction Step 2

The reaction step 2 is the step of allowing the compound represented by Formula (3) obtained from the reaction step 1 to react with the imidazole compound represented by Formula (4) to give the unsaturated carboxylic acid amide compound represented by Formula (1).

The imidazole compound represented by Formula (4) may be used in an amount of typically from about 0.5 to about 20.0 times, preferably from 0.8 to 8.0 times, particularly preferably from 1.0 to 3.0 times, the mole of the compound represented by Formula (3). The imidazole compound represented by Formula (4), if used in an amount greater than the range, may readily impair the reaction operability and economic efficiency. In contrast, the imidazole compound represented by Formula (4), if used in an amount less than the range, may cause the unsaturated carboxylic acid amide compound represented by Formula (1) to be prepared in a lower yield.

The reaction may be performed in the presence of, or in the absence of, a solvent. The solvent is exemplified by ester solvents such as ethyl acetate, butyl acetate, and isobutyl acetate; saturated or unsaturated hydrocarbon solvents such as pentane, hexane, heptane, octane, and petroleum ether; aromatic hydrocarbon solvents such as benzene, toluene, and xylenes; halogenated hydrocarbon solvents such as methylene chloride, chloroform, 1,2-dichloroethane, chlorobenzene, and bromobenzene; ether solvents such as diethyl ether, diisopropyl ether, dibutyl ether, tetrahydrofuran, dioxane, 1,2-dimethoxyethane, and cyclopentyl methyl ether; nitrile solvents such as acetonitrile and benzonitrile; sulfoxide solvents such as dimethyl sulfoxide; sulfolane solvents such as sulfolane; amide solvents such as dimethylformamide; and high-boiling solvents such as silicone oils. Each of them may be used alone or in combination. In particular in the present invention, the reaction step 2 is preferably performed in the presence of the same solvent as in the reaction step 1. Specifically, both the reaction step 1 and the reaction step 2 are preferably performed in the presence of an ester solvent. This eases the concentration control of a solvent in crystallization (in particular, poor-solvent crystallization) in the purification step and can give a high-purity crystal.

The solvent may be used in an amount of typically from about 1 to about 100000 parts by weight, and preferably from 1 to 10000 parts by weight, per 1 part by weight of the compound represented by Formula (3), whereas the amount is not critical within such a range as to allow the dissolution or dispersion of reactants and as not to impair properties such as economic efficiency. The solvent used in the reaction step 1 may be used commonly as a solvent in the reaction step 2. In this case, the solvent used in the reaction step 1 may be used in the reaction step 2 as intact or after adjusting the concentration by concentrating or diluting after the completion of the reaction step 1.

The reaction in the reaction step 2 may be performed at a temperature of typically from about −50° C. to 150° C., preferably from −10° C. to 80° C., and particularly preferably from 10° C. to 50° C. The reaction may be performed under any of a pressure (under a load), normal atmospheric pressure, and reduced pressure (typically from about 0.0001 to about 0.1 MPa, and preferably from 0.001 to 0.1 MPa). The reaction is often performed under normal atmospheric pressure or reduced pressure. The reaction may be performed according to any system selected from batch, semi-batch, and continuous systems.

In the reaction step 2, an acidic gas (hydrogen chloride) and/or an amine hydrochloride gas is by-produced with reaction progress. In a preferred embodiment of the present invention, these substances are preferably removed so as to accelerate the reaction progress and to inhibit the formation of by-products such as chlorine-containing compound. A way to remove these substances is exemplified by a method of adding a base so as to trap or scavenge the substances, where the base is inert to the reaction or does not affect the obtaining of the target product; and a method of performing the reaction while separating the substances from the reaction system continuously or discontinuously (batchwise) by a separation process such as degassing, extraction, distillation, rectification, molecular distillation, and/or adsorption. The separation operation may be performed under either of reduced pressure and normal atmospheric pressure.

The base that is inert to the reaction or does not affect the obtaining of the target product is exemplified by inorganic bases such as sodium hydrogencarbonate, sodium carbonate, potassium carbonate, potassium hydrogencarbonate, sodium hydroxide, and potassium hydroxide; aromatic amines such as pyridine; primary amines such as methylamine, ethylamine, propylamine, isopropylamine, allylamine, butylamine, pentylamine, hexylamine, octylamine, 2-ethylhexylamine, benzylamine, cyclopentylamine, cyclohexylamine, aniline, toluidine, xylidine, naphthylamine, and 2-aminothiazole; secondary amines such as dimethylamine, diethylamine, dipropylamine, diisopropylamine, diallylamine, dibutylamine, dipentylamine, dioctylamine, di(2-ethylhexyl) amine, ethylenimine, pyrrolidine, piperidine, piperazine, morpholine, N-methylaniline, diphenylamine, phenothiazine, and pyrazole; and tertiary amines such as triethylamine, and tributylamine. Each of them may be used alone or in combination. The base may be used in an amount of typically from about 0.5 to about 10.0 times, and preferably from 0.8 to 3.0 times, the mole of the compound represented by Formula (3).

Purification Step

A reaction product obtained from the reaction step 2 is subsequently subjected to the purification step. The purification step may employ a separation process such as filtration, concentration, distillation, extraction, crystallization, adsorption, recrystallization, or column chromatography, or a separation process of any combination of them.

In a preferred embodiment of the present invention, chlorine-containing compounds are preferably separated and removed using an adsorbent. The adsorbent usable herein is exemplified by silica gel, alumina, activated carbon, magnesia, and hydrotalcite. Among them, silica gel is preferred herein for its excellent separation and/or removal efficiency. Most preferably, the chlorine-containing compounds are separated and removed using silica gel column chromatography.

In the present invention, the reaction product is washed with water as added to the reaction system, is dehydrated, and then subjected to crystallization, where the dehydration is performed to a water content of 2.0 percent by weight or less, preferably 1.8 percent by weight or less, more preferably 1.6 percent by weight or less, furthermore preferably 1.5 percent by weight or less, particularly preferably 1.0 percent by weight or less, and most preferably 0.5 percent by weight or less. The lower limit of the water content is 0 percent by weight. The present invention performs the operations and can give a crystal that has such properties as to be resistant to scattering and attachment to the vessel wall and still resistant to hydrolysis even when subjected to a drying process. The dehydration before crystallization, if performed insufficiently, may give a crystal that readily scatters, is easily attached to the vessel wall, and often suffers from losses. In addition, this crystal has a high water content, is thereby susceptible to hydrolysis upon long-time drying treatment, and is hardly prevented from deterioration in quality upon industrial production.

In an embodiment, the reaction solvent after the completion of the reaction step 2 is separated and recovered by distillation, and a crystallization solvent is newly added to perform the crystallization. In another embodiment, the reaction solvent is used as the crystallization solvent to perform the crystallization.

The crystallization solvent is exemplified by saturated or unsaturated hydrocarbon solvents such as pentane, hexane, heptane, octane, and petroleum ether; ketones such as methyl ethyl ketone; ester solvents such as methyl acetate, ethyl acetate, isopropyl acetate, and butyl acetate; aromatic hydrocarbon solvents such as benzene, toluene, and xylenes; and ether solvents such as diethyl ether, diisopropyl ether, dibutyl ether, tetrahydrofuran, dioxane, 1,2-dimethoxyethane, and cyclopentyl methyl ether. Alcohols and water cause the unsaturated carboxylic acid amide compound represented by Formula (1) to decompose and are not preferred herein. In a preferred embodiment of the present invention, the reaction solvent may be used as intact as the crystallization solvent. This is preferred for a more easy/simple operation and for higher economical efficiency.

The crystallization solvent may be used in an amount of typically from about 1 to about 20 times, and preferably from 1 to 15 times, the weight of the unsaturated carboxylic acid represented by Formula (2).

The crystallization may be performed by any process such as concentration crystallization, poor-solvent crystallization, and cooling crystallization alone or in combination.

In a preferred embodiment upon poor-solvent crystallization, the reaction solvent (e.g., ester solvent) is used as intact as a good solvent, and a hydrocarbon solvent is used as a poor solvent, where the hydrocarbon solvent is exemplified by hexane, cyclohexane, and heptane. The ratio (by weight) of the good solvent to the poor solvent is typically from about 1:0.5 to about 1:5, and preferably from 1:1 to 1:3.

The crystallization may be performed at a temperature of typically from about −5° C. to about 70° C.; and preferably from 10° C. to 50° C. upon concentration crystallization, or preferably from 0° C. to 10° C. upon cooling crystallization.

The crystallization may be performed for a time of typically from about 3 to about 24 hours, whereas the time may be adjusted as appropriate depending on the reactor scale.

Crystals crystallized by the crystallization operation may be separated and recovered from the crystallization solvent by filtration. The solvent contained in the recovered crystals may be removed by heat drying.

The crystal obtained by the production method contains the unsaturated carboxylic acid amide compound represented by Formula (1) in an amount of 95 percent by area or more, preferably 98 percent by area or more, particularly preferably 99 percent by area or more, and most preferably 99.5 percent by area or more. The crystal, if containing the unsaturated carboxylic acid amide compound represented by Formula (1) in a content less than the range, may be used with difficulty as a high-performance material. The content of the unsaturated carboxylic acid amide compound represented by Formula (1) in the crystal may be measured using high-performance liquid chromatography under analysis conditions as follows.

High-Performance Liquid Chromatographic Analysis Conditions

Column: INERTSIL® ODS3

Mobile phase:
Component "A": 50 mM $KH_2PO_4/K_2HPO_4$ (pH=7) aqueous solution
Component "B": acetonitrile
Pump mode: isocratic (A:B=50%:50% (v/v))
UV wavelength: 220 nm
Injection volume: 5 μm
Column temperature: 40° C.
Flow rate: 1.0 mL/min.

The crystal may have a content of chlorine-containing compounds of preferably about 1000 ppm or less, more preferably 800 ppm or less, furthermore preferably 500 ppm or less, particularly preferably 100 ppm or less, and most preferably 50 ppm or less, of the total amount of the crystal. The content of chlorine-containing compounds may be measured typically using combustion ion chromatography.

The crystal obtained by the production method may have a bulk density of typically from 0.05 to 0.30 g/mL, and preferably from 0.10 to 0.20 g/mL.

As used herein the term "bulk density" refers to the ratio of the mass of an untapped (i.e., loose) powder sample to its volume including the contribution of the interparticulate void volume. The bulk density depends on both the density of powder particles and the spatial arrangement of particles in the powder bed. The "bulk density" in the present invention may be determined in the following manner. Into a dry 250-mL graduated cylinder (readable to 2 mL), approximately 100 g ($W_0$ in gram) of a sample weighed with 0.1% accuracy is gently introduced without compacting. The volume ($V_0$ in mL) is read to the nearest graduated unit. The bulk density is calculated by the formula:

Bulk density (g/mL)=$W_0/V_0$

In X-ray diffraction, the crystal according to the present invention obtained by the method exhibits a peak at 2θ in the range of from 29.0 to 30.0 and a peak at 2θ in at least one range selected from the group consisting of 6.0 to 8.0, 12.0 to 13.5, and 16.5 to 17.5 and exhibits approximately no peak at 2θ in the range of from 14.0 to 15.0. In a preferred embodiment, the crystal exhibits at least one peak at 2θ in each of the ranges of 6.0 to 8.0, 12.0 to 13.5, 16.5 to 17.5, and 29.0 to 30.0.

The crystal according to the present invention contains the unsaturated carboxylic acid amide compound represented by Formula (1) with a high purity and exhibits the characteristic peaks in X-ray diffraction, is thereby resistant to scattering, and can be handled easily. In addition, the crystal is resistant to attachment to the vessel wall and less suffers from losses that are caused by the attachment of the crystal to the vessel wall. For these reasons, the crystal according to the present invention is advantageously usable as or for high-performance materials such as photosensitive high-performance materials (resist materials) for use in the production of electrical and electronic components. In particular, the crystal is advantageously usable as or for materials requiring high reliability, such as semiconductor encapsulating materials, packaging materials typically for semiconductor devices and MEMS (micro electro mechanical systems), and photosensitive materials for semiconductor devices, liquid crystal displays, and MEMS.

EXAMPLES

The present invention will be illustrated in further detail with reference to several examples below. It should be noted, however, that the examples are by no means intended to limit the scope of the present invention.

Example 1

In a 1.5-m³ reactor, 105 kg of 4-methoxycinnamic acid and 462 kg of ethyl acetate were placed to give a suspension. The suspension was combined with 73.6 kg of thionyl chloride (1.05 times the mole of 4-methoxycinnamic acid) added dropwise while maintaining the reactor inside temperature at 65° C. to 70° C. After the dropwise addition, a reaction was performed until the conversion from 4-methoxycinnamic acid reached 99% or more. After the completion of reaction, about 200 kg of ethyl acetate was distilled off together with unreacted thionyl chloride and an acidic gas at 60° C. under reduced pressure. After the concentration by distillation, the mixture was combined with ethyl acetate in an amount equal to the distilled-off amount and yielded 579.6 kg of a 4-methoxycinnamoyl chloride/ethyl acetate solution (1).

Next, 52.2 kg of imidazole (1.3 times the mole of 4-methoxycinnamoyl chloride), 59.6 kg of triethylamine (1.0 time the mole of 4-methoxycinnamoyl chloride), and 824.2 kg of ethyl acetate were placed in a 3-m³ reactor, followed by mixing. After checking the dissolution of imidazole, the mixture was combined with the 4-methoxycinnamoyl chloride/ethyl acetate solution (1) added dropwise while maintaining the reactor inside temperature at 10° C. to 30° C.

After completion of dropwise addition, the resulting mixture was further stirred for one hour, combined and washed with 525 kg of ion-exchanged water, and separated to give an organic layer. The resulting organic layer was subsequently washed with 525 kg of a 8% sodium hydrogencarbonate aqueous solution and further washed twice with 525 kg of ion-exchanged water. The resulting organic layer was dehydrated by reflux of an upper portion to a water content in the system of 1.2 percent by weight, from which about 650 kg of ethyl acetate was distilled off by vacuum concentration. The resulting organic layer was adjusted to a temperature of 40° C., combined with about 650 kg of heptane (in an amount corresponding to 1 part by weight of heptane per 1 part by weight of ethyl acetate), subsequently cooled down to 5° C. or lower, separated using a centrifuge, and yielded about 110 kg of wet crystals. The wet crystals were dried at 30° C. under reduced pressure using a conical dryer and yielded 103.4 kg of crystals including 1-(3-(4-methoxyphenyl)acryloyl)-imidazole with a purity of 99.7 percent by area. The crystals had a content of chlorine-containing compounds of less than 10 ppm. The crystals constituted a yellowish white powder and had a bulk density of 0.15 g/mL. The crystals were low-dusting and little suffered from losses due to attachment to the conical dryer.

Figure 1:
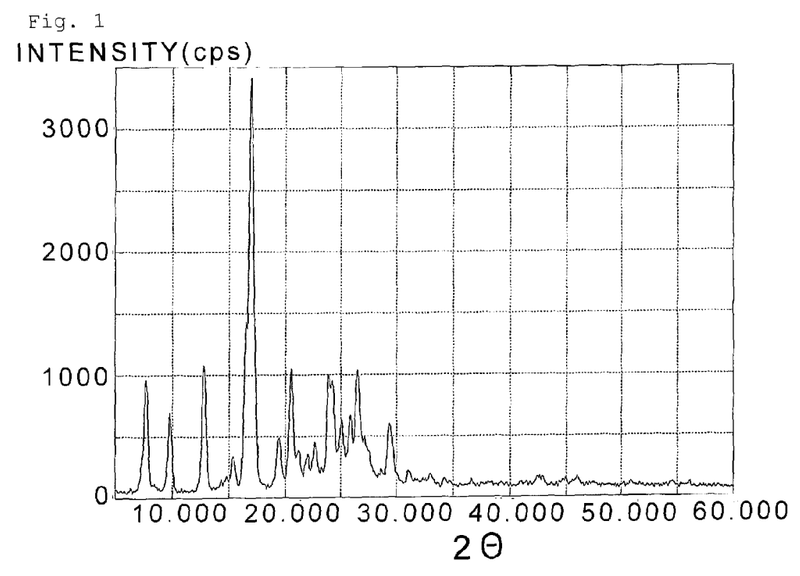
FIG. 1 is an X-ray diffraction (XRD) chart of crystals prepared in Example 1.

In addition, the crystals were subjected to structural analysis by X-ray diffractometry (XRD). The result is indicated in FIG. 1. The data demonstrate that representative X-ray diffraction peaks were detected at 2θ of 6.3, 12.6, 17.1, and 29.4, and that no peak was detected at 2θ in the range of from 14.0 to 15.0.

Example 2

In a 55-L reactor, 2.5 kg of 4-methoxycinnamic acid and 11 kg of ethyl acetate were placed to give a suspension. The suspension was combined with 1.75 kg of thionyl chloride (1.05 times the mole of 4-methoxycinnamic acid) added dropwise while maintaining the reactor inside temperature at 65° C. to 70° C. After the dropwise addition, a reaction was performed until the conversion from 4-methoxycinnamic acid reached 99% or more. After the completion of reaction, about 5 kg of ethyl acetate was distilled off together with unreacted thionyl chloride and an acidic gas at 60° C. under reduced pressure. After the concentration, the resulting mixture was combined with ethyl acetate in an amount equal to the distilled-off amount and yielded 15.2 kg of a 4-methoxycinnamoyl chloride/ethyl acetate solution (2).

Next, in the 55-L reactor after the completion of washing, 1.24 kg of imidazole (1.3 times the mole of 4-methoxycinnamoyl chloride), 1.42 kg of triethylamine (1.0 time the mole of 4-methoxycinnamoyl chloride), and 19.6 kg of ethyl acetate were placed, followed by mixing to give a mixture. After checking the dissolution of imidazole, the mixture was combined with the 4-methoxycinnamoyl chloride/ethyl acetate solution (2) added dropwise while maintaining the reactor inside temperature at 10° C. to 30° C.

After the completion of dropwise addition, the resulting mixture was further stirred for one hour, combined and washed with 12.5 kg of ion-exchanged water, and separated to give an organic layer. The resulting organic layer was subsequently washed with 12.5 kg of a 8% sodium hydrogencarbonate aqueous solution and further washed twice with 12.5 kg of ion-exchanged water. The resulting organic layer was concentrated to be dehydrated, combined with ethyl acetate in an amount equal to the distilled-off amount to adjust the water content in the system to 1.4 percent by weight, and vacuum concentration was performed to distill off 15.5 kg of ethyl acetate. The resulting organic layer was adjusted to a temperature of 40° C., combined with 15.5 kg of heptane (in an amount corresponding to 1 part by weight of heptane per 1 part by weight of ethyl acetate), subsequently cooled down to 5° C. or lower, filtrated, and yielded 3.5 kg of wet crystals. The wet crystals were dried at 30° C. under reduced pressure on an evaporator and yielded 2.7 kg of crystals including 1-(3-(4-methoxyphenyl)acryloyl)-imidazole with a purity of 99.9 percent by area. The crystals had a content of chlorine-containing compounds of less than 10 ppm.

The crystals constituted a yellowish white powder and had a bulk density of 0.18 g/mL. The crystals were low-dusting and little suffered from losses due to attachment to the flask.

The crystals were subjected to structural analysis by X-ray diffractometry (XRD) and gave a result as in FIG. 1.

Example 3

In a 100-mL three-neck flask, 3.1 g of 4-methoxycinnamic acid and 14.0 g of ethyl acetate were placed to give a suspension. The suspension was combined with 2.2 g of thionyl chloride (1.05 times the mole of 4-methoxycinnamic acid) added dropwise while maintaining the reactor inside temperature at 65° C. to 70° C. After the dropwise addition, a reaction was performed until the conversion from 4-methoxycinnamic acid reached 99% or more. After completion of reaction, 6.1 g of ethyl acetate was distilled off together with unreacted thionyl chloride and an acidic gas at 60° C. under reduced pressure. After the concentration, the resulting mixture was combined with ethyl acetate in an amount equal to the distilled-off amount and yielded 19.2 g of a 4-methoxycinnamoyl chloride/ethyl acetate solution (3).

Next, in a 200-mL three-neck flask, 1.3 g of imidazole (1.3 times the mole of 4-methoxycinnamoyl chloride), 1.8 g of triethylamine (1.0 time the mole of 4-methoxycinnamoyl chloride), and 25.1 g of ethyl acetate were placed, followed by mixing to give a mixture. After checking the dissolution of imidazole, the mixture was combined with the 4-methoxycinnamoyl chloride/ethyl acetate solution (3) added dropwise while maintaining the reactor inside temperature at 10° C. to 30° C. After the completion of dropwise addition, the resulting mixture was further stirred for one hour, combined and washed with 15.5 g of ion-exchanged water, and separated to give an organic layer. The organic layer was subsequently washed with 15.5 g of a 8% sodium hydrogencarbonate aqueous solution and further washed twice with 15.5 g of ion-exchanged water. The resulting organic layer was concentrated to be dehydrated, combined with ethyl acetate in an amount equal to the distilled-off amount to adjust the water content in the system to 0.3 percent by weight, from which 18.5 g of ethyl acetate was distilled off by vacuum concentration. The resulting organic layer was adjusted to a temperature of 40° C., combined with 18.5 g of heptane (in an amount corresponding to 1 part by weight of heptane per 1 part by weight of ethyl acetate), subsequently cooled down to 5° C. or lower, filtrated, and yielded 4.1 g of wet crystals. The wet crystals were dried at 30° C. under reduced pressure on an evaporator and yielded 3.0 g of crystals including 1-(3-(4-methoxyphenyl)acryloyl)-imidazole with a purity of 99.2 percent by area. The crystals had a content of chlorine-containing compounds of less than 10 ppm.

The crystals constituted a yellowish white powder and had a bulk density of 0.30 g/mL.

The crystals were subjected to structural analysis by X-ray diffractometry (XRD) and gave a result as in FIG. 1.

Comparative Example 1

The procedure of Example 3 was performed, except for not subjecting an organic layer (having a water content of 3.5 percent by weight) obtained by washing and separation to dehydration treatment, and yielded crystals including 1-(3-(4-methoxyphenyl)acryloyl)-imidazole with a purity of 99.1 percent by area. The crystals had a content of chlorine-containing compounds of less than 10 ppm.

The obtained crystals had a bulk density of 0.29 g/mL.

Figure 2:
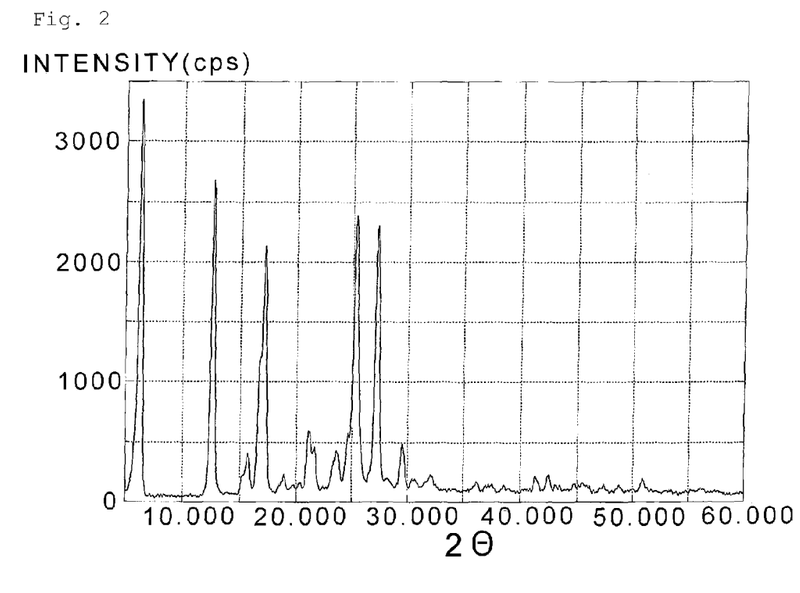
FIG. 2 is an X-ray diffraction (XRD) chart of crystals prepared in Comparative Example 1.

The crystals were subjected to structural analysis by X-ray diffractometry (XRD) and gave a result as indicated in FIG. 2. FIG. 2 demonstrates that the obtained crystals were different from the crystals obtained in Examples 1 to 3.

The purities of the crystals obtained in the examples and the comparative example were determined in a manner as follows. An aliquot (0.04 to 0.05 g) of crystals to be tested was weighed, diluted (combined) with acetonitrile (for high-performance liquid chromatograph use, supplied by Wako Pure Chemical Industries, Ltd.) in a measuring cylinder to 25 mL total to give a sample. The sample was subjected to high-performance liquid chromatography to give a chromatograph. Peak areas of components observed on the chromatogram were measured, and the percentage (%) of the peak area of the target compound based on the total sum of the peak areas of all the components observed on the chromatogram was calculated to give a purity.

The high-performance liquid chromatographic analysis was performed under conditions as follows.

Analysis Conditions:
Column: INERTSIL® ODS3
Mobile phase:
Component "A": 50 mM $KH_2PO_4/K_2HPO_4$ (pH=7) aqueous solution
Component "B": acetonitrile
Pump mode: isocratic (A:B=50%:50% (v/v))
UV wavelength: 220 nm
Injection volume: 5 μm
Column temperature: 40° C.
Flow rate: 1.0 mL/min.

The X-ray diffractometry (XRD) of the crystals obtained in the examples and comparative example was performed using an apparatus under conditions as follows.

X-ray diffractometer: MiniFlex II (trade name) supplied by Rigaku Corporation
X-ray source: Cu Kα radiation, 30 kV, 15 mA
Scan rate: 4.00/min
Divergence slit: 0.625
Scattering slit: 1.25

INDUSTRIAL APPLICABILITY

The crystal according to the present invention has a high purity and has such properties as to be resistant to scattering and attachment to the vessel wall. The production method according to the present invention can produce the crystal having the properties stably even upon industrial production. The crystal according to the present invention is therefore particularly useful as raw materials for industrial products. The crystal is advantageously useful typically as or for pharmaceuticals, agricultural chemicals, polymeric materials, intermediates of them, and high-performance materials such as photosensitive high-performance materials (resist materials) for use in the production of electrical and electronic components. In particular, the crystal is advantageously usable as or for materials requiring high reliability, such as semiconductor encapsulating materials, packaging materials typically for semiconductor devices and MEMS (micro electro mechanical systems), and photosensitive materials for semiconductor devices, liquid crystal displays, and MEMS.

The invention claimed is:
1. A crystal comprising
an unsaturated carboxylic acid amide compound represented by Formula (1) in an amount of 95 percent by area or more,
in X-ray diffraction, the crystal exhibiting a peak at 2θ of 29.0 to 30.0 and a peak at 2θ in at least one range selected from the group consisting of 6.0 to 8.0, 12.0 to 13.5, and 16.5 to 17.5 and exhibiting approximately no peak at 2θ in a range of 14.0 to 15.0,
Formula (1) expressed as follows:

[Chem. 1]

(1)

wherein $R^1$ to $R^5$ are identical or different groups independently selected from hydrogen, alkyl, hydroxyl, alkoxy, and nitro, where at least two of $R^1$ to $R^5$ may be linked to form a ring together with carbon atoms constituting the specified aromatic ring; and $R^6$, $R^7$, and $R^8$ are identical or different groups independently selected from hydrogen, alkyl, and aryl, where $R^7$ and $R^8$ may be linked to form a ring together with carbon atoms constituting the specified imidazole ring,
the amount of the unsaturated carboxylic acid amide compound represented by Formula (1) being measured by high-performance liquid chromatography under analysis conditions as follows:
column: INERTSIL® ODS3
a mobile phase comprising:
a 50 mM $KH_2PO_4/K_2HPO_4$ (pH=7) aqueous solution as a component "A"; and acetonitrile as a component "B",
pump mode: isocratic (A:B=50%:50% (v/v)),
UV wavelength: 220 nm,
injection volume: 5 μm,
column temperature: 40° C., and
flow rate: 1.0 mL/min.
2. The crystal according to claim 1 wherein the unsaturated carboxylic acid amide compound comprises at least one compound selected from the group consisting of compounds represented by Formulae (1-1) to (1-6):

[Chem. 2]

(1-1)

(1-2)

(1-3)

(1-4)

(1-5)

(1-6)

3. A method for producing a crystal, the method comprising the steps of:
a) chlorinating an unsaturated carboxylic acid represented by Formula (2) with thionyl chloride to give a compound represented by Formula (3);
b) allowing the prepared compound represented by Formula (3) to react with an imidazole compound represented by Formula (4) to give an unsaturated carboxylic acid amide compound represented by Formula (1) as a reaction product; and
c) purifying the reaction product to give the crystal according to claim 1,
the step a) being performed in the presence of an ester solvent,
the method comprising at least one of:
using the thionyl chloride in an amount of from 0.5 to 3.0 times the mole of the unsaturated carboxylic acid represented by Formula (2) in the step a); and
separating and removing a chlorine-containing compound using an adsorbent in the step c),
the step c) comprising the successive substeps of:
adding water to a reaction system to wash the reaction product;

dehydrating the reaction product to a water content of 2.0 percent by weight or less; and subjecting the reaction product to crystallization, Formulae (2), (3), (4), and (1) expressed as follows:

[Chem. 3]

(2)

wherein $R^1$ to $R^5$ are identical or different groups independently selected from hydrogen, alkyl, hydroxyl, alkoxy, and nitro, where at least two of $R^1$ to $R^5$ may be linked to form a ring together with carbon atoms constituting the specified aromatic ring,

[Chem. 4]

(3)

wherein $R^1$ to $R^5$ are as defined above,

[Chem. 5]

(4)

wherein $R^6$, $R^7$, and $R^8$ are identical or different groups independently selected from hydrogen, alkyl, and aryl, where $R^7$ and $R^8$ may be linked to form a ring together with carbon atoms constituting the specified imidazole ring,

[Chem. 6]

(1)

wherein $R^1$ to $R^8$ are as defined above.

4. A method for producing a crystal, the method comprising the steps of:

a) chlorinating an unsaturated carboxylic acid represented by Formula (2) with thionyl chloride to give a compound represented by Formula (3);

b) allowing the prepared compound represented by Formula (3) to react with an imidazole compound represented by Formula (4) to give an unsaturated carboxylic acid amide compound represented by Formula (1) as a reaction product; and c) purifying the reaction product to give the crystal according to claim 2, the step a) being performed in the presence of an ester solvent, the method comprising at least one of:

using the thionyl chloride in an amount of from 0.5 to 3.0 times the mole of the unsaturated carboxylic acid represented by Formula (2) in the step a); and separating and removing a chlorine-containing compound using an adsorbent in the step c), the step c) comprising the successive substeps of:

adding water to a reaction system to wash the reaction product;

dehydrating the reaction product to a water content of 2.0 percent by weight or less; and subjecting the reaction product to crystallization, Formulae (2), (3), (4), and (1) expressed as follows:

[Chem. 3]

(2)

wherein $R^1$ to $R^5$ are identical or different groups independently selected from hydrogen, alkyl, hydroxyl, alkoxy, and nitro, where at least two of $R^1$ to $R^5$ may be linked to form a ring together with carbon atoms constituting the specified aromatic ring,

[Chem. 4]

(3)

wherein $R^1$ to $R^5$ are as defined above,

[Chem. 5]

(4)

wherein $R^6$, $R^7$, and $R^8$ are identical or different groups independently selected from hydrogen, alkyl, and aryl, where $R^7$ and $R^8$ may be linked to form a ring together with carbon atoms constituting the specified imidazole ring,

[Chem. 6]

(1)

wherein $R^1$ to $R^8$ are as defined above.

* * * * *